US007990610B2

(12) United States Patent
Higuchi et al.

(10) Patent No.: US 7,990,610 B2
(45) Date of Patent: Aug. 2, 2011

(54) STEREOMICROSCOPE WITH REPOSITIONING ASSISTANT'S MICROSCOPE

(75) Inventors: Katsuhiro Higuchi, Tokyo (JP); Hiroshi Akiyama, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 451 days.

(21) Appl. No.: 12/289,781

(22) Filed: Nov. 4, 2008

(65) Prior Publication Data

US 2009/0116102 A1    May 7, 2009

(30) Foreign Application Priority Data

Nov. 7, 2007   (JP) ................................. 2007-289427

(51) Int. Cl.
*G02B 21/22* (2006.01)
(52) U.S. Cl. ........................................ 359/377; 359/384
(58) Field of Classification Search .......... 359/372–378, 359/381, 384
See application file for complete search history.

(56) References Cited

U.S. PATENT DOCUMENTS

| 4,123,151 | A | * | 10/1978 | Aurin | 359/861 |
| 4,143,938 | A | * | 3/1979 | Feinbloom | 359/363 |
| 4,783,159 | A | * | 11/1988 | Takagi et al. | 359/377 |
| 5,530,587 | A | * | 6/1996 | Sander et al. | 359/376 |
| 5,898,518 | A | * | 4/1999 | Biber | 359/385 |
| 6,081,371 | A | * | 6/2000 | Shioda et al. | 359/372 |
| 6,473,229 | B2 | * | 10/2002 | Nakamura | 359/377 |
| 7,379,239 | B2 | * | 5/2008 | Strobel et al. | 359/384 |
| 2004/0120031 | A1 | | 6/2004 | Fukaya et al. | |
| 2004/0252371 | A1 | | 12/2004 | Sturgis et al. | |
| 2006/0023300 | A1 | * | 2/2006 | Sander | 359/376 |
| 2006/0098274 | A1 | * | 5/2006 | Kitajima | 359/385 |
| 2008/0100893 | A1 | * | 5/2008 | Knuenz et al. | 359/196 |
| 2009/0268281 | A1 | * | 10/2009 | Schnitzler et al. | 359/377 |

FOREIGN PATENT DOCUMENTS

| DE | 3229516 A1 | * | 2/1984 |
| DE | 195 41 420 A1 | | 5/1996 |
| EP | 1 486 159 A1 | | 12/2004 |
| JP | 04355712 A | * | 12/1992 |
| JP | 2000-330032 | | 11/2000 |
| JP | 2000330032 A | * | 11/2000 |
| JP | 2004-226828 | | 8/2004 |
| JP | 2005-137577 | | 6/2005 |
| JP | 2006284989 A | * | 10/2006 |

OTHER PUBLICATIONS

European Search Report issued Feb. 23, 2009 in EP 08 01 8660.

* cited by examiner

*Primary Examiner* — Mark Consilvio
(74) *Attorney, Agent, or Firm* — Edwards Angell Palmer & Dodge LLP

(57) ABSTRACT

An illumination optical system projects an illumination light onto an observation object via an objective lens. A first observation optical system guides the illumination light reflected by the observation object to a first ocular lens. A second observation optical system includes a second ocular lens for observing the reflected light of the illumination light. An optical system drive mechanism rotates the second observation optical system and arranges the second observation optical system between a first position and second position facing each other. A reflecting member is disposed at a position retracted from the illumination light path and the reflected light path and reflects the reflected light in a direction different from the optical axis. A drive mechanism rotates the reflecting member around a rotation axis orthogonal to the optical axis and guides the reflected light to the second observation optical system arranged at the first or second position.

7 Claims, 10 Drawing Sheets

STEREOMICROSCOPE WITH REPOSITIONING ASSISTANT'S MICROSCOPE

BACKGROUND OF THE INVENTION

1. Field of the Invention

The present invention relates to a stereomicroscope, and particularly relates to a stereomicroscope by which two observers can simultaneously observe an object.

2. Description of the Related Art

In general, a stereomicroscope is a microscope that enables observation of an object as it is without processing it into a thinly sliced specimen, etc. Some stereomicroscopes enable two observers to observe an object simultaneously. An example of such a stereomicroscope is a surgical microscope used in the medical field (particularly in the ophthalmology, neurosurgery, etc.).

Japanese Unexamined Patent Application Publications Nos. 2000-330032, 2004-226828 and 2005-137577 disclose conventional stereomicroscopes (surgical microscopes). The stereomicroscopes described in Japanese Unexamined Patent Application Publications Nos. 2000-330032 and 2004-226828 each have an operator's microscope and an assistant's microscope. The assistant's microscope is disposed rotatably around the center of an objective lens with respect to the operator's microscope.

Part of an optical system of the stereomicroscope is shown in FIGS. 13 and 14. A stereomicroscope 1000 is an apparatus for observing a magnified image of an observation object 2000. The stereomicroscope 1000 comprises a primary observation optical system 1010 and a secondary observation optical system 1020 as well as an illumination optical system, which is not shown.

In a surgical microscope, the primary observation optical system 1010 is an optical system of a microscope used by the operator. Further, the secondary observation optical system 1020 is an optical system for an assistant's microscope used by an assistant. In FIG. 13, the operator is on the rear of paper (behind an objective lens 1001) and observes the observation object 2000 while facing the front of the paper. The assistant is on the right or left side of the operator. The illumination optical system is placed on the front side of the paper of FIG. 13.

The illumination optical system is an optical system for projecting an illumination light onto the observation object 2000. The illumination optical system includes a reflecting mirror 1031 shown in FIG. 14, and additionally includes optical elements, which are not shown, such as a light source, an aperture and a lens. The reflecting mirror 1031 is placed immediately above the objective lens 1001. The reflecting mirror 1031 reflects an illumination light outputted from the light source, and projects it onto the observation object 2000 via the objective lens 1001.

The primary observation optical system 1010 guides the illumination light reflected by the observation object 2000 to an operator's ocular lens (not shown). The primary observation optical system 1010 is provided with a pair of optical systems on the right and left. Thus, stereoscopic observation with both eyes becomes possible.

The primary observation optical system 1010 is provided with variable magnification lenses (zoom lenses) 1021L and 1021R, and additionally, various kinds of optical elements, which are not shown.

The secondary observation optical system 1020 guides the illumination light reflected by the observation object 2000 to an assistant's ocular lens (not shown). The secondary observation optical system 1020 is also provided with a pair of optical systems on the right and left, whereby stereoscopic observation with both eyes becomes possible. The secondary observation optical system 1020 is provided with various kinds of optical members such as a reflecting member 1022 provided immediately above the periphery of the objective lens 1001 and a lens 1021.

The primary observation optical system 1010 is placed so that right and left optical axes OL and OR become parallel to an optical axis O of the objective lens 1001 (at least adjacent to the objective lens 1001). In addition, the secondary observation optical system 1020 is placed so that an optical axis OP thereof becomes orthogonal to the optical axis O of the objective lens 1001.

The secondary observation optical system 1020 is configured so that the position thereof with respect to the primary observation optical system 1010 can be changed in order to enable the assistant to change his/her position. To be specific, the secondary observation optical system 1020 is configured so as to be rotatable around the optical axis O of the objective lens 1001. The secondary observation optical system 1020 rotates around the optical axis O along a trajectory T shown in FIG. 14. Thus, the assistant can observe while being on the right or left side of the operator. Symbols FL and FR in FIG. 14 denote observation fields by the right and left optical systems of the primary observation optical system 1010.

Further, in some conventional stereomicroscopes, right and left observation fields of the primary observation optical system are arranged asymmetrically with respect to the center of the objective lens, and a reflecting member (equivalent to the abovementioned reflecting member 1022) that guides a reflected light from an observation object to the secondary observation optical system is arranged in the center of the objective lens.

Further, Japanese Unexamined Patent Application Publication No. 2005-37577 discloses a stereomicroscope configured so that the secondary observation optical system itself is capable of swiveling upward and thereby the observation position of the assistant can be switched to the right and left.

The conventional stereomicroscopes as described above have the following problems.

Firstly, regarding the stereomicroscope shown in FIGS. 13 and 14, when the secondary observation optical system 1020 is rotated, the reflecting member and a member that supports it may block the observation fields FL and FR of the operator.

Further, in some stereomicroscopes, the secondary observation optical system 1020 is configured to be attachable to and detachable from a lens tube 1040. It takes time and labor to manually change the position of the secondary observation optical system 1020, and moreover, the structure of an attachment/detachment part is complicated.

Further, regarding the stereomicroscope in which the right and left observation fields of the primary observation optical system are arranged asymmetrically with respect to the center of the objective lens, the observation object is observed from an oblique direction. Therefore, a burden may be imposed on the operator.

Further, regarding the stereomicroscopes in which the secondary observation optical system is configured to be capable of swiveling upward, the shape of the lens tube of the primary observation optical system is limited, and a complicated rotating mechanism is required.

Additionally, since various instruments are installed in an observation room such as an operating room, the swiveling secondary observation optical system may hit objects and people.

SUMMARY OF THE INVENTION

The present invention was devised in order to solve the aforementioned problems, and an object of the present invention is to provide a stereomicroscope that enables easy change of the position of an assistant's optical system without blocking an observation field of a primary observer.

A first aspect of the present invention provides a stereomicroscope, comprising: an objective lens; an illumination optical system configured to project an illumination light onto an observation object via the objective lens; a first observation optical system configured to guide the illumination light reflected by the observation object and propagated through the objective lens to a first ocular lens; a second observation optical system including a second ocular lens for observing the reflected light of the illumination light propagated through the objective lens; an optical system drive mechanism configured to rotate the second observation optical system around an axis parallel to an optical axis of the objective lens, thereby switching and placing the second observation optical system between a first position and a second position facing each other; a reflecting member disposed at a position retracted from both a light path of the illumination light projected onto the observation object and a light path of the reflected light entering the first observation optical system, and configured to reflect the reflected light propagated through the objective lens in a direction different from the optical axis; and a reflecting member drive mechanism configured to rotate the reflecting member around a rotation axis orthogonal to the optical axis and guide the reflected light propagated through the objective lens to the second observation optical system placed at the first position or the second position.

A second aspect of the present invention provides the stereomicroscope according to Claim 1, wherein: the reflecting member has a reflecting face that is disposed obliquely to a plane including the optical axis, and that reflects the reflected light propagated through the objective lens; and the reflecting member drive mechanism rotates the reflecting member so that the reflecting face is placed at symmetrical positions with respect to the plane.

A third aspect of the present invention provides the stereomicroscope according to Claim 2, wherein: the reflecting member has a slope that is disposed so that an upper end substantially contacts the plane, and that slants from the upper end toward an edge of the objective lens; the reflecting face is disposed to the slope; and the reflecting member drive mechanism rotates the reflecting member while taking an intersection line of the plane and a plane that passes a lower end of the slope and that is orthogonal to the plane as the rotation axis, thereby placing the reflecting face at the symmetrical positions.

A fourth aspect of the present invention provides the stereomicroscope according to Claim 2, wherein: the reflecting member has a slope with an upper end and a lower end placed on a side opposite to the plane; the reflecting face is disposed to the slope; and the reflecting member drive mechanism rotates the reflecting member while taking an intersection line of the plane and the slope as the rotation axis, thereby placing the reflecting face at the symmetrical positions.

A fifth aspect of the present invention provides the stereomicroscope according to Claim 1, wherein: the reflecting member drive mechanism rotates the reflecting member in conjunction with switching of a position of the second observation optical system by the optical system drive mechanism.

A sixth aspect of the present invention provides the stereomicroscope according to Claim 5, wherein: the optical system drive mechanism has a first gear that is disposed along a rotation direction of the second observation optical system and rotates with the second observation optical system; and the reflecting member drive mechanism has an axial member that is disposed along the rotation axis and connected to the reflecting member, and a second gear that is connected to the axial member and engaged with the first gear to rotate the axial member with the reflecting member in accordance with rotation of the first gear.

A seventh aspect of the present invention provides the stereomicroscope according to Claim 1, wherein: the second ocular lens includes a pair of right and left ocular lenses; the second observation optical system includes a left observation optical system that guides the illumination light propagated through the objective lens to the left ocular lens, and a right observation optical system that guides the illumination light to the right ocular lens; the reflecting member has a pair of right and left reflecting faces; and the reflecting member drive mechanism rotates the reflecting member, thereby guiding the reflected light reflected by the left reflecting face to the left observation optical system, and guiding the reflected light reflected by the right reflecting face to the right observation optical system.

The stereomicroscope according to the present invention has the first observation optical system and the second observation optical system. Here, the first observation optical system is used by a primary observer, and the second observation optical system is used by another observer (an assistant). The second observation optical system is rotatable around the axis parallel to the optical axis of the objective lens, and is positioned so as to switch between the first position and second position facing each other.

Further, the stereomicroscope according to the present invention is provided with the reflecting member that reflects a reflected light of an illumination light reflected by an observation object and propagated through the objective lens, in a direction different from the optical axis of the objective lens. The reflecting member is disposed at a position retracting from the light path of the illumination light travelling toward the observation object and the light path of the reflected light that enters the first observation optical system.

Furthermore, the stereomicroscope according to the present invention is provided with a reflecting member drive mechanism that rotates the reflecting member around the rotation axis orthogonal to the optical axis of the objective lens and guides the reflected light reflected by the observation object and propagated through the objective lens to the second observation optical system positioned at the first position or the second position.

According to the stereomicroscope configured as described above, it is possible to rotate the reflecting member around the rotational axis orthogonal to the optical axis of the objective lens.

Therefore, it is possible to change the position of the second observation optical system without blocking the observation field of a primary observer.

DETAILED DESCRIPTION OF THE PREFERRED EMBODIMENTS

An embodiment of a stereomicroscope according to the present invention will be described in detail with reference to the drawings. In the embodiment described below, an ophthalmologic surgical microscope will be described as a specific example of the stereomicroscope. The configuration described in the embodiment described below can also be applied appropriately to stereomicroscopes other than this stereomicroscope.

[Appearance]

Figure 1:
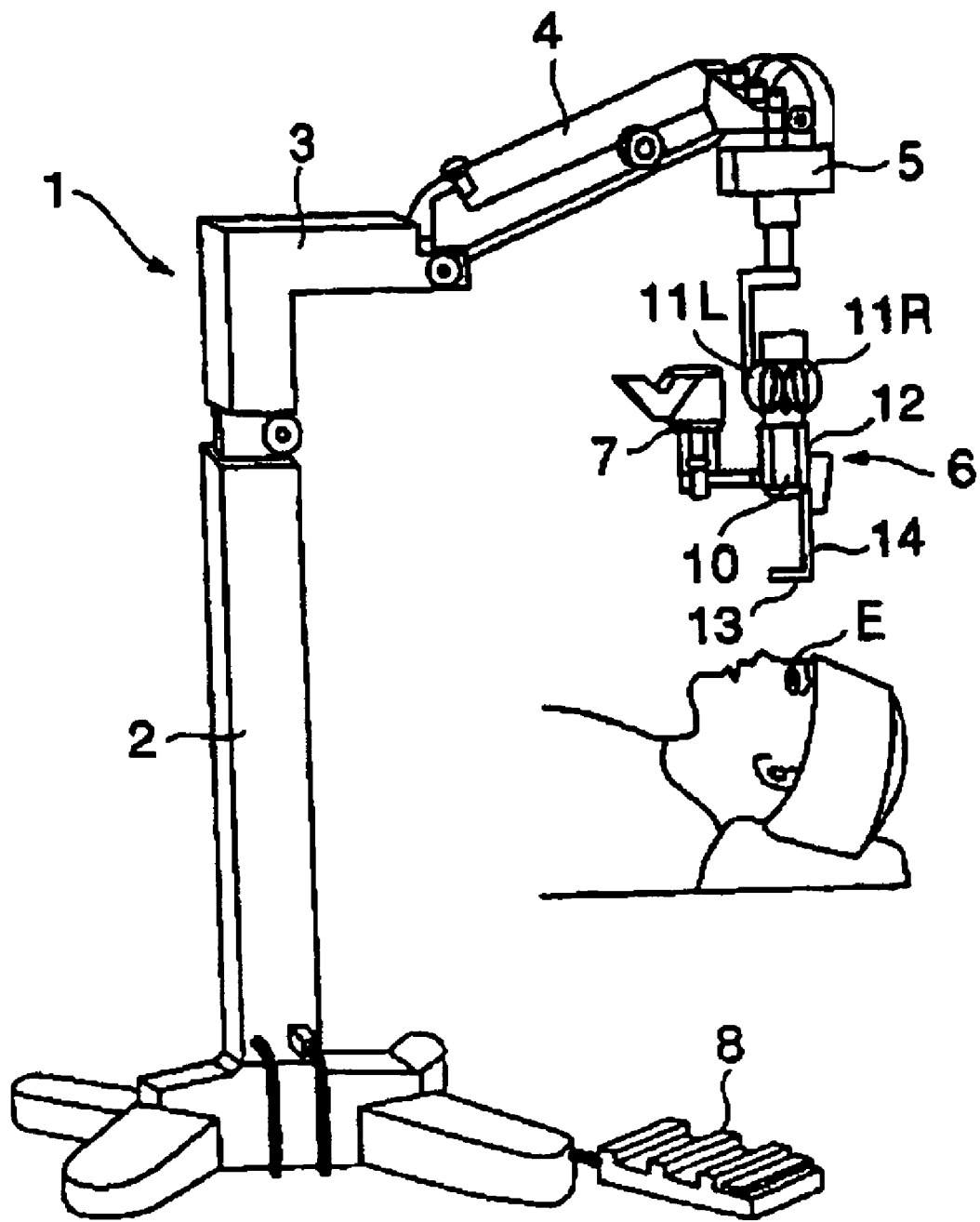
FIG. 1 is a schematic view illustrating an example of the appearance of an embodiment of a stereomicroscope (surgical microscope) according to the present invention.

Firstly, with reference to FIGS. 1 through 3, the appearance of a surgical microscope according to this embodiment will be described. A surgical microscope 1 is used for observing a surgical field during a surgery of an eye E.

One end of a first arm 3 is connected to the upper end of a supporting post 2 of the surgical microscope 1. One end of a second arm 4 is connected to the other end of the first arm 3. A drive unit 5 is connected to the other end of the second arm 4. An operator's microscope 6 is suspended from the drive unit 5. An assistant's microscope 7 is disposed together with the operator's microscope 6.

The surgical microscope 1 is provided with a foot switch 8. The operator makes the surgical microscope 1 execute a desired operation by operating the foot switch 8 with his/her foot. The drive unit 5 3-dimensionally moves the operator's microscope 6 and the assistant's microscope 7 in response to the operation with the foot switch 8, etc.

The drive unit 5 includes an actuator such as a motor.

Various kinds of optical systems and drive systems are housed in a lens tube part 10 of the operator's microscope 6. An inverter part 12 is disposed at the upper part of the lens tube part 10. The inverter part 12 is an optical unit that converts an inverted image into an erected image. Right and left eyepieces 11L and 11R are disposed at the upper part of the inverter part 12. Each of the eyepieces 11L and 11R is provided with an ocular lens (described later). Moreover, an objective lens 15 is disposed at the lower end of the lens tube part 10.

The upper end of a holding arm 14 is connected to the operator's microscope 6. A head lens 13 is held at the lower end of the holding arm 14. The head lens 13 focuses an illumination light and illuminates the inside of the eye E. As the head lens 13, a plurality of lenses having different refractive powers (e.g., 40D, 80D, and 120D) are prepared and selectively attached to the holding arm 14.

The upper end of the holding arm 14 is pivotally disposed so as to be capable of revolving in the vertical direction. Thus, the head lens 13 can be inserted into and removed from a position between the eye E and the objective lens 15. A position where the head lens 13 is inserted (a using position) is a position on the optical axis of the objective lens 15 and between the anterior focal position of the objective lens 15 and the eye E.

The head lens 13 is held by a holding plate 141a formed so as to encompass the head lens 13. The holding plate 141a is connected to an arm part 141 via an axis 141b, and is rotatable around the axis 141b. A slanting part 141c is formed on the holding plate 141a.

A coil spring 154 is wound around the upper end of the arm part 141. The upper end of the arm part 141 is pivotally disposed to one end of a housing part 174 by an axis 174a. The arm part 141 is provided with an operating knob (not shown) extending horizontally when viewed from the operator side. By grasping this operating knob and swiveling the holding arm 14 around the axis 174a, the operator can position the head lens 13 to the using position described before and to a housing position described later.

A main body 6a of the operator's microscope 6 has a driver 175. To the driver 175, an up-and-down arm 171 is connected via a supporting member 176. At the upper end of the up-and-down arm 171, a fringe part 171a is formed to prevent the up-and-down arm 171 from falling off the supporting member 176. The driver 175 vertically moves the up-and-down arm 171 together with the supporting member 176. At this moment, the head lens 13 is moved integrally with the up-and-down arm 171.

A connecting part 171b is connected to the lower end of the up-and-down arm 171. An elevation restraining member 172 is connected to the connecting part 171b. The elevation restraining member 172 contacts an elevation restraining member 177 on the side of the main body 6a when the up-and-down arm 171 is elevated to a specified position. Thus, the elevation restraining members 172, 177 act so as to prevent the up-and-down arm 171 from moving upward more than the specified position.

A coupling knob 173 is disposed to the connecting part 171b.

When the coupling knob 173 is rotated in a specified direction, the tip of a rotating screw (not shown) is fitted into a coupling hole 177a. Thus, the head lens 13, the holding arm 14, the housing part 174, etc., are coupled to the main body 6a. In this coupling state, movement of the head lens 13, etc. is inhibited.

The housing part 174 is connected to the elevation restraining member 172. The housing part 174 houses the holding arm 14 (and the head lens 13). FIG. 3 shows a state in which the holding arm 14 is housed. On the lower face of the housing part 174, a concave housing part is formed along the longitudinal direction of the housing part 174.

The holding arm 14 is swiveled around the axis 174a and thereby housed into the housing part.

Figure 3:
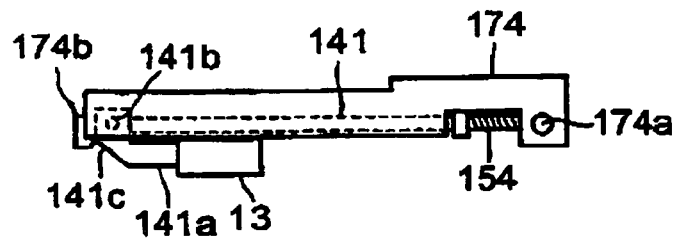
FIG. 3 is schematic view illustrating an example of the appearance of the embodiment of the stereomicroscope (surgical microscope) according to the present invention.

In the state in which the holding arm 14 is housed, as shown in FIG. 3, the lens faces of the head lens 13 are directed in the vertical direction. This is because of the action of the slanting part 141c of the holding plate 141a and a contacting member 174b attached to the end of the housing part 174. That is, when the arm part 141 is swiveled upward around the axis 174a, the slanting part 141c comes in contact with the contacting member 174b, and the holding plate 141a is guided along the slanting part 141c to rotate around the axis 141b.

Consequently, the head lens 13 is positioned in the housing position in a state as shown in FIG. 3.

Figure 2:
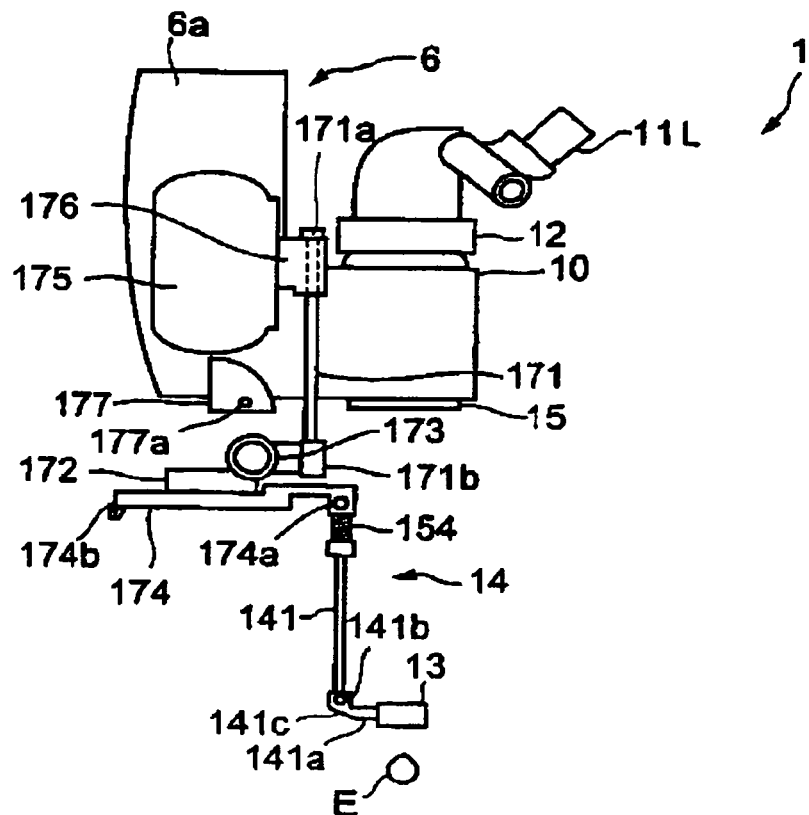
FIG. 2 is schematic view illustrating an example of the appearance of the embodiment of the stereomicroscope (surgical microscope) according to the present invention.

On the other hand, FIG. 2 shows the head lens 13 placed in the using position between the eye E and the objective lens 15. To house the head lens 13 from this state, the operator grasps the abovementioned operating knob and swivels the holding arm 14 upward, thereby housing the head lens 13 and the holding arm 14 into the housing part 174. By swiveling the holding arm 14 downward in a reverse manner, it is possible to place the housed head lens 13 at the using position.

The housing part 174 is formed so as to be attachable to and detachable from the elevation restraining member 172. This is for removing the head lens 13 and the holding arm 14 from the operator's microscope 6 when sterilizing them. A part including the housing part 174 and the head lens 13 is integrally composed. In a state in which the head lens 13, etc., are removed, the surgical microscope 1 can be used as a surgical microscope without the head lens 13.

[Configuration of Optical System]

Figure 4:
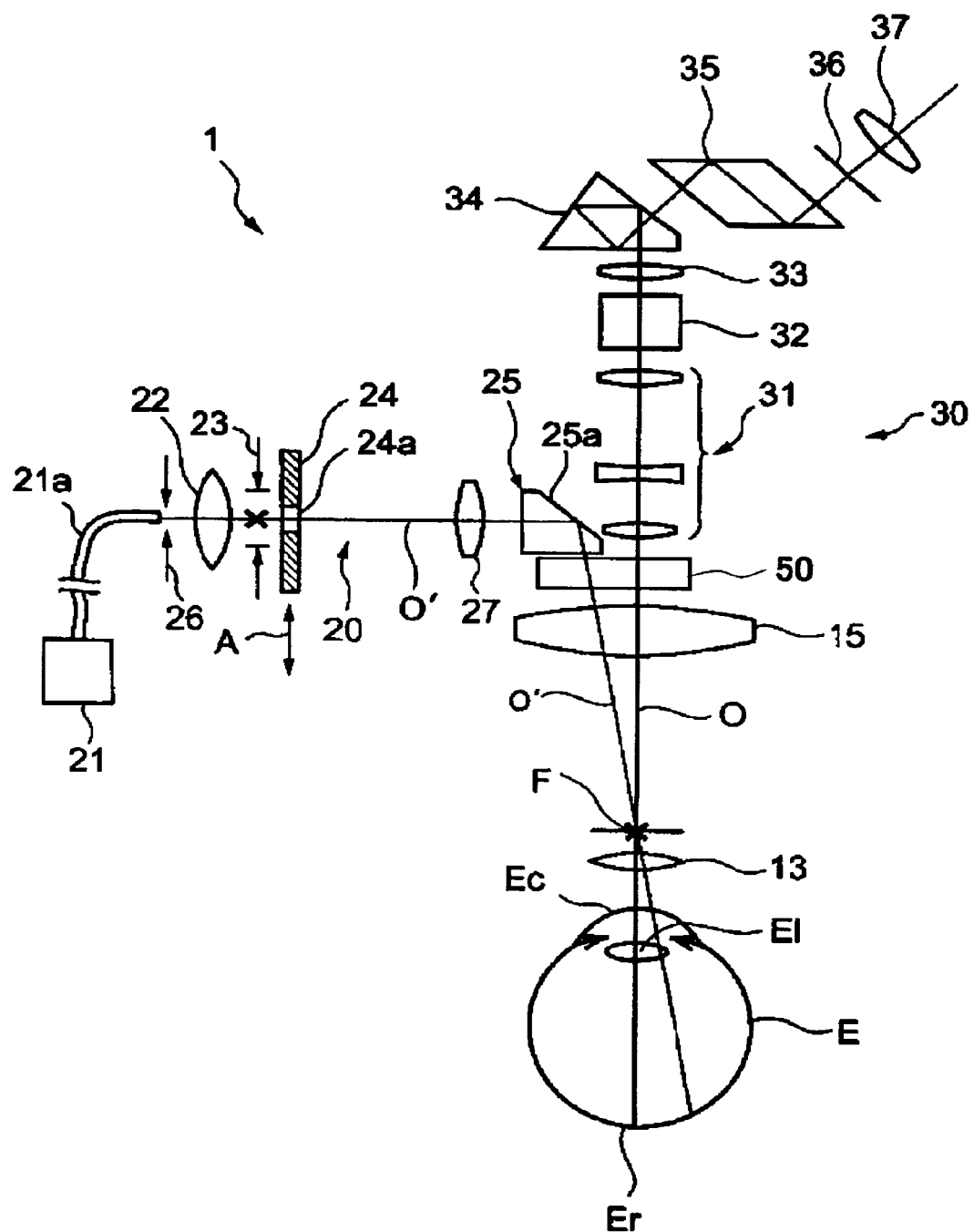
FIG. 4 is a schematic view illustrating an example of the configuration of an optical system of the embodiment of the stereomicroscope (surgical microscope) according to the present invention.
Figure 5:
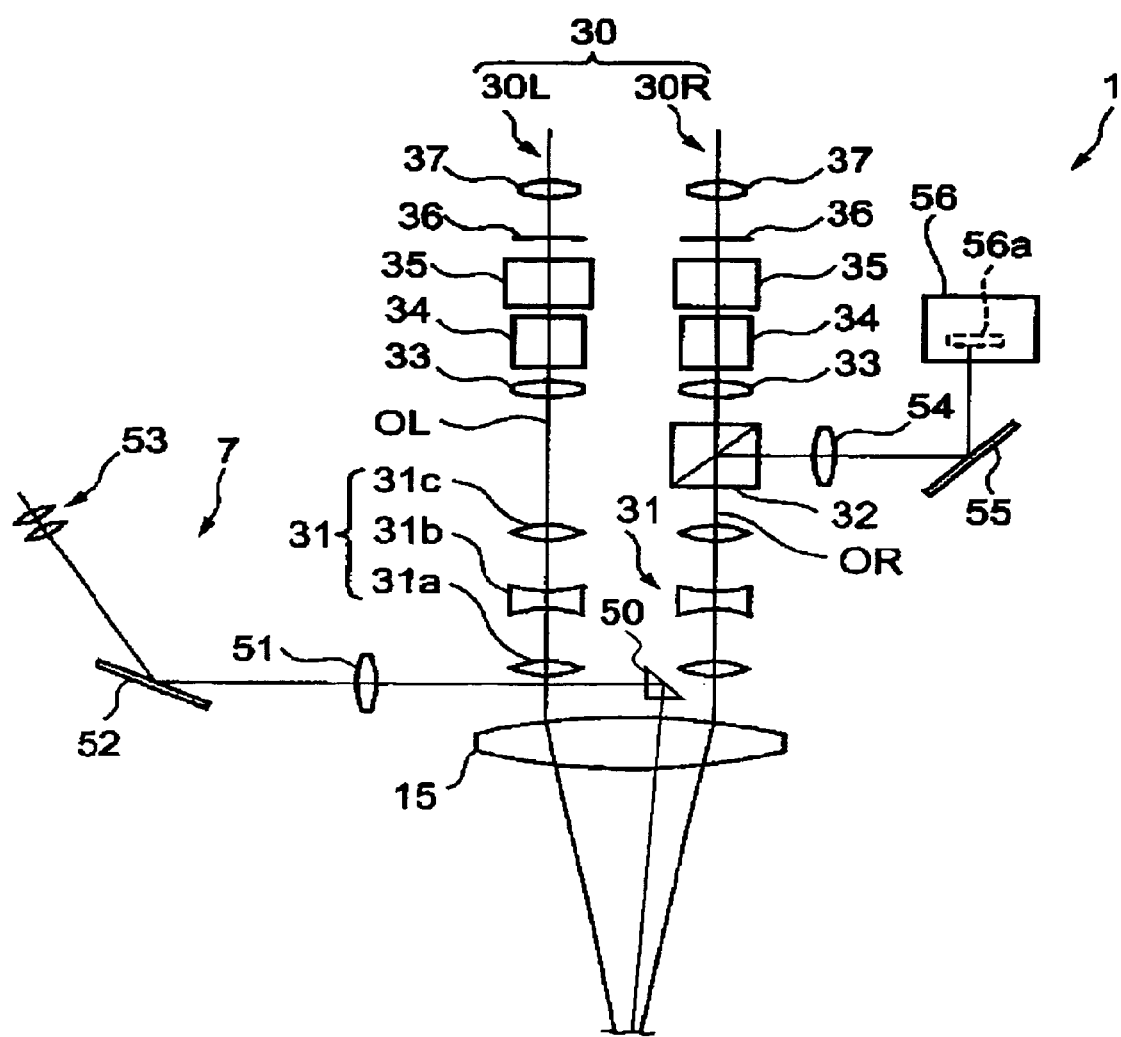
FIG. 5 is a schematic view illustrating an example of the configuration of an optical system of the embodiment of the stereomicroscope (surgical microscope) according to the present invention.

Next, with reference to FIGS. 4 through 8, an optical system of the surgical microscope 1 will be described. Here, FIG. 4 is a view of the optical system when viewed from the left side by the operator. FIG. 5 is a view of the optical system viewed from the operator's side. In this embodiment, the vertical direction, the horizontal direction, the anteroposterior direction, etc., are directions viewed from the operator's side, unless stated otherwise. Regarding the vertical direction, a direction from the objective lens 15 to an observation object (the eye E) is the downward direction, and the opposite is the upward direction.

{Observation Optical System}

An observation optical system 30 is an example of the "first observation optical system" of the present invention. A pair of observation optical systems 30 are disposed on the right and left as shown in FIG. 5. The observation optical system 30L on the left side is referred to as a left observation optical system. The observation optical system 30R on the right side is referred to as a right observation optical system. Symbol OL denotes the optical axis (the observation optical axis) of the left observation optical system 30L. Symbol OR denotes the optical axis (the observation optical axis) of the right observation optical system 30R. The right and left observation optical systems 30R and 30L are arranged to sandwich the optical axis O of the objective lens 15.

Each of the right and left observation optical systems 30R and 30L has a zoom lens system 31, a beam splitter 32 (only the right observation optical system 30R), an imaging lens 33, an image-erecting prism 34, an interpupillary adjustment prism 35, a field diaphragm 36, and an ocular lens 37. The zoom lens system 31 includes a plurality of zoom lenses 31a, 31b and 31c.

The beam splitter 32 of the right observation optical system 30R separates part of an observation light guided along the observation optical axis OR from the eye E, and guides it to a TV-camera imaging system. This TV-camera imaging system includes an imaging lens 54, a reflecting mirror 55, and a TV camera 56.

The TV camera 56 has an imaging device 56a. The imaging device 56a is composed of, for example, a CCD (Charge Coupled Devices) image sensor, or a CMOS (Complementary Metal Oxide Semiconductor) image sensor. As the imaging device 56a, a device with a 2-dimensional light receiving face is used, for example.

When the surgical microscope 1 is in use, a light receiving face of the imaging device 56a is positioned, for example, at a position optically conjugate with the surface of a cornea Ec, or at a position optically conjugate with a position that is one half of the corneal curvature radius distant from the corneal apex in the depth direction.

The assistant's microscope 7 is a microscope used by the assistant assisting the operator. The assistant's microscope 7 is provided with an optical system (assistant's optical system) forming right and left observation light paths through the objective lens 15. The assistant's optical system includes an imaging lens 51, a reflecting mirror 52, and an ocular lens 53, as shown in FIG. 5.

The reflecting member 50 is disposed at a position above the objective lens 15 and near the center of the objective lens 15. An observation light from the eye E enters the reflecting member 50 through the objective lens 15, is reflected by the reflecting face, and is guided to the assistant's microscope 7. The observation light having entered the assistant's microscope 7 is collected by the right and left imaging lenses 51, is reflected by the right and left reflecting mirrors 52, and is guided to the right and left ocular lenses 53. An entrance pupil of the optical system of the assistant's microscope 7 is formed on the reflecting face of the reflecting member 50.

A dedicated zoom lens system may be disposed to the assistant's microscope 7, though illustration thereof is omitted. In this case, it is desirable to interlock a zoom magnification of the assistant side with a zoom magnification of the operator side (a zoom magnification by the zoom lens system 31).

{Illumination Optical System}

An illumination optical system 20 includes an illumination light source 21, an optical fiber 21a, an emission diaphragm 26, a condenser lens 22, an illumination field diaphragm 23, a slit plate 24, a collimator lens 27, and an illumination prism 25 as shown in FIG. 4.

The illumination field diaphragm 23 is disposed at a position optically conjugate with an anterior focal position F of the objective lens 15. Moreover, a slit hole 24a of the slit plate 24 is formed at a position substantially optically conjugate with the anterior focal position F. In addition, at the time of observation of the eye E, the vertical position of the lens tube part 10 is adjusted so that the anterior focus position F of the objective lens 15 is conjugate with a fundus oculi Er.

The illumination light source 21 is disposed outside the lens tube part 10 of the operator's microscope 6. One end of an optical fiber 21a is connected to the illumination light source 21. The other end of the optical fiber 21a is arranged at a position facing a condenser lens 22 within the lens tube part 10. An illumination light outputted from the illumination light source 21 is guided by the optical fiber 21a to enter the condenser lens 22.

An emission diaphragm 26 is provided at a position facing the emission opening of the optical fiber 21a (a fiber end on the side of the condenser lens 22). The emission diaphragm 26 acts so as to shield a partial region of the emission opening of the optical fiber 21a. When a region shielded by the emission diaphragm 26 is changed, an emission region of the illumination light is changed. Consequently, it is possible to change a projection angle by the illumination light, i.e., an angle formed by the incident direction of the illumination light into the eye E, and the optical axis O of the objective lens 15, for example.

A slit plate 24 is provided with a plurality of slit holes 24a having a shape according to the shape of a reflecting face 25a of the illumination prism 25. The slit plate 24 is composed of a disc-shaped member having a light-shielding effect. Thus, the slit plate 24 acts so as to generate an illumination light with a specified shape of cross-section.

Further, the slit plate 24 is moved in a direction orthogonal to an illumination optical axis O' (a direction of an arrow A shown in FIG. 4) by a drive mechanism, which is not shown, thereby being inserted into and removed from the illumination optical axis O'.

The collimator lens 27 makes the illumination light having propagated through the slit hole 24a into a parallel light flux. The illumination light having become a parallel light flux is reflected on the reflecting face 25a of the illumination prism 25 to enter the objective lens 15, and is further propagated through the head lens 13 to enter the eye E.

The illumination light projected onto the eye E propagates through the cornea Ec and enters the eye. At this moment, part of the illumination light is reflected by the cornea Ec. The illumination light having entered the eye is applied to a crystalline lens El and a fundus oculi Er and then reflected thereby.

The reflected light of the illumination light by the eye E (the cornea Ec, the crystalline lens El, the fundus oculi Er, etc.), which will be referred to as an observation light hereafter, enters an observation optical system 30 via the head lens 13 and the objective lens 15. At this moment, part of the observation light is reflected by a reflecting member 50 to enter an optical system of the assistant's microscope 7 (an assistant's optical system). This configuration enables the operator and the assistant to observe a magnified image of the eye E.

[Mode of Guiding Observation Light]

Figure 6:
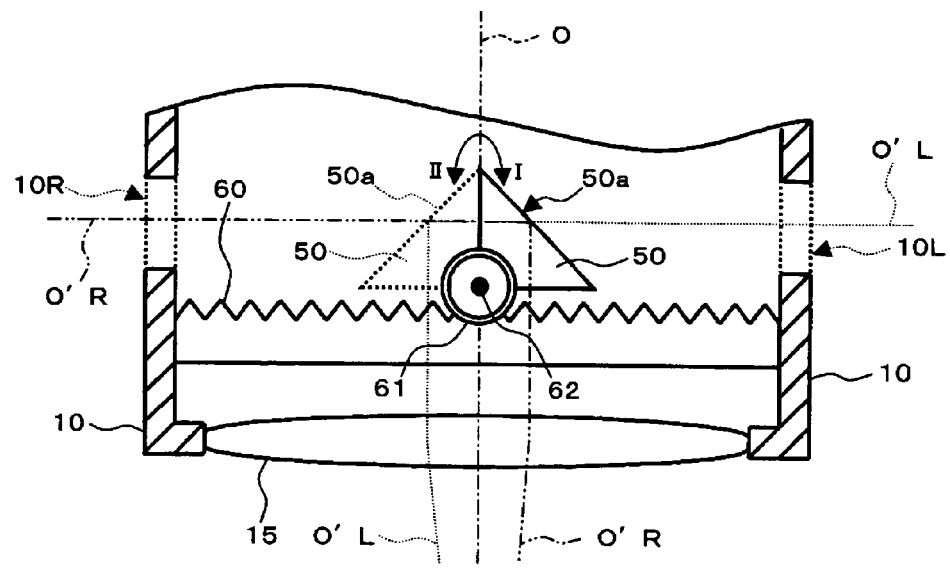
FIG. 6 is a schematic view illustrating an example of the configuration of an optical system of the embodiment of the stereomicroscope (surgical microscope) according to the present invention.
Figure 7:
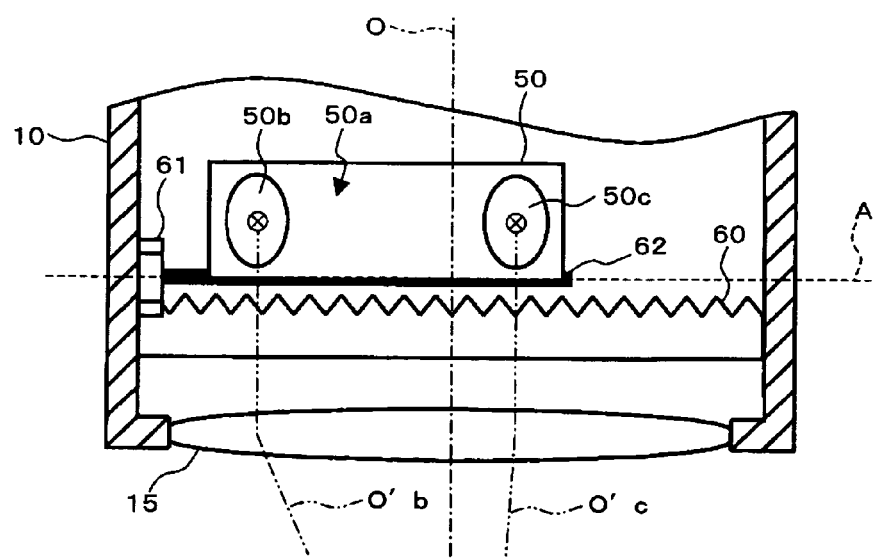
FIG. 7 is a schematic view illustrating an example of the configuration of an optical system of the embodiment of the stereomicroscope (surgical microscope) according to the present invention.
Figure 8:
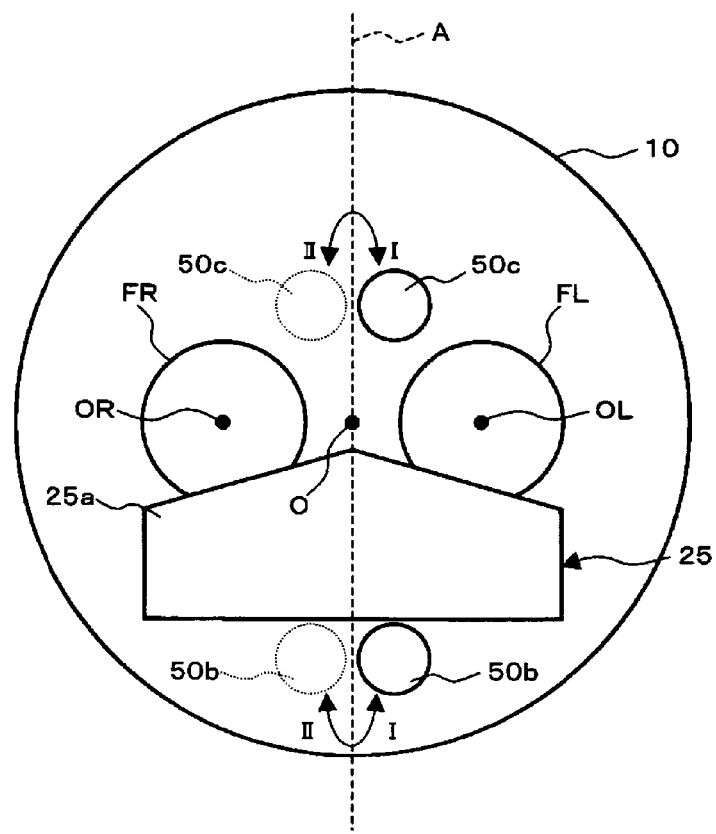
FIG. 8 is a schematic view illustrating an example of the configuration of an optical system of the embodiment of the stereomicroscope (surgical microscope) according to the present invention.

Referring to FIGS. 6 to 8, a configuration of guiding an observation light to the assistant's microscope 7 will be described. Here, FIG. 6 is a view taken from the opposite side of the operator (from the side of the illumination optical system 20). FIG. 7 is a view taken from the opposite side of the assistant's microscope 7 (from the left side of the operator). FIG. 8 is a view taken from above. In FIGS. 6 and 7, only the lens tube part 10 is shown in cross-section.

As shown in FIGS. 6 and 7, the reflecting member 50 is formed so that, assuming a direction connecting the operator side and the side of the illumination optical system 20 is a longer direction, the cross-section in a shorter direction has a shape of a triangular prism of a right triangle. As shown with an arrow indicating both sides in FIGS. 6 and 8, the arrangement state of the reflecting member 50 is switched between a state shown with a symbol "I" and a state shown with a symbol "II."

In the arrangement state shown with the symbol "I," the reflecting member 50 having a shape of a triangular prism has an end face on the operator side, an end face on the side of the illumination optical system 20, a first side face that extends upwardly from a right angle part of the abovementioned cross-section, a second side face that extends horizontally from the right angle part, and a slope 50a that opposes the right angle part. When the reflecting member 50 is brought into the arrangement state shown with the symbol "II," the first side face is placed in the horizontal direction, and the second side face is placed in the vertical direction. At this moment, the slope 50a turns 90°.

The slope 50a is provided with two reflecting faces 50b and 50c.

The reflecting face 50b is disposed on the side of the illumination optical system 20, and the reflecting face 50c is disposed on the operator side. Each of the reflecting faces 50b and 50c acts so as to reflect a light applied to the inner side of the slope 50a. Each of the reflecting faces 50b and 50c can be composed of, for example, a mirror that is fixed to the slope 50a so as to face the inner side of the reflecting member 50.

An axial member 62 is fixed to the right angle part of the reflecting member 50. The end of the axial member 62 on the side of the illumination optical system 20 is fixed to a gear 61. The gear 61 and the axial member 62 are disposed so as to be capable of integrally rotating around a rotational axis A shown in FIGS. 7 and 8.

Part of the lens tube part 10 is formed into a cylindrical shape with the vertical direction as the axis. Part of the lens tube part 10 (at least a part shown in FIGS. 6 and 7) is capable of being horizontally rotated together with the assistant's microscope 7 by a mechanism similar to a conventional one (an optical system drive mechanism). At least the eyepieces 11L and 11R are configured not to rotate together with the assistant's microscope 7.

On the lens tube part 10, holes 10L and 10R for guiding the observation light to the assistant's microscope 7 (the assistant's optical system) are formed. The hole 10L is for guiding the observation light to the assistant's microscope 7 placed left as seen from the operator, and the hole 10R is for guiding the observation light to the assistant's microscope 7 placed right as seen from the operator.

On the inner wall face of the lens tube part 10, a gear 60 with teeth aligned along the circumferential direction is disposed. The gear 60 is fixed to the inner wall face of the lens tube part 10. As seen from above, the gear 60 is disposed like a circle or an arc on the inner wall face of the lens tube part 10. The gear 60 has teeth on the upper face thereof. The teeth on the outer circumferential face of the gear 61 are engaged with the teeth of the gear 60.

With this configuration, when the assistant's microscope 7 is rotated, (part of) the lens tube part 10 and the gear 60 rotate integrally therewith, the gear 61 engaged with the gear 60 rotates with the axial member 62, and the reflecting member 50 rotates with the axial member 62 around the axis A.

Here, the reflecting member 50 rotates from the state of the symbol "I" to the state of the symbol "II" or from the state of the symbol "II" to the state of the symbol "I" in accordance with the rotation direction of the assistant's microscope 7, for example.

In a specific example, when the assistant's microscope 7 is moved from left to right in FIG. 6 (i.e., moved from right to left as seen from the operator), the reflecting member 50 moves from the state of the symbol "I" to the state of the symbol "II." Conversely, when the assistant's microscope 7 is moved from right to left in FIG. 6 (i.e., moved from left to right as seen from the operator), the reflecting member 50 moves from the state of the symbol "II" to the state of the symbol "I." Here, the assistant's microscope 7 rotates via the opposite side of the operator, i.e., the side of the illumination optical system 20.

In this embodiment, the assistant's microscope 7 and the lens tube part 10 are configured to rotate integrally. However, it is possible to configure so that the assistant's microscope 7 rotates relative to the lens tube part 10. In this case, the gear 60 is disposed not on the inner wall face of the lens tube part 10 but on a site rotating with the assistant's microscope 7, along the rotation direction. Additionally, in this case, the central axis of rotation of the assistant's microscope 7 does not need to coincide with the optical axis O of the objective lens 15. However, in order to rotate the assistant's microscope 7 in the horizontal direction (namely, in order to rotate the assistant's microscope 7 within a plane orthogonal to the optical axis O), it is desired to place the central axis in parallel to the optical axis O. In a case where the assistant's microscope 7 is rotated within a plane that tilts from the horizontal direction, the central axis does not need to be parallel to the optical axis O.

[Operation]

Figure 9:
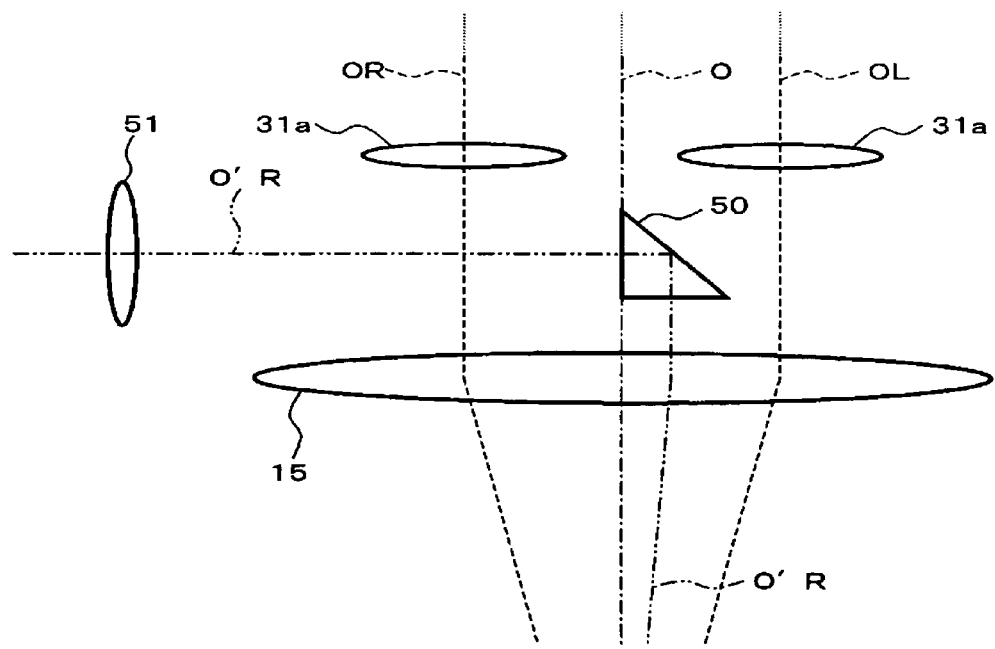
FIG. 9 is a schematic view for explaining an operation of the embodiment of the stereomicroscope (surgical microscope) according to the present invention.
Figure 10:
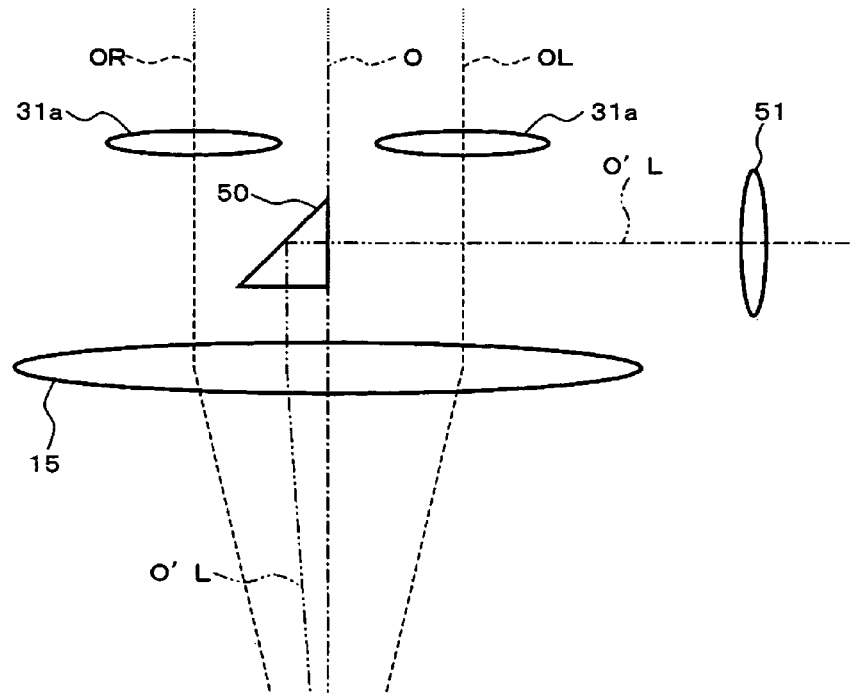
FIG. 10 is a schematic view for explaining the operation of the embodiment of the stereomicroscope (surgical microscope) according to the present invention.

Further referring to FIGS. 9 and 10, the operation of the surgical microscope 1 will be described. FIGS. 9 and 10 are views of the optical system near the reflecting member 50, taken from the side of the illumination optical system 20.

FIG. 9 illustrates an aspect of the optical system when the assistant's microscope 7 is arranged on the right side as viewed by the operator. In this case, as shown by a solid line in FIGS. 6 and 8, the reflecting member 50 is situated on the left side of the slope optical axis O.

The reflected light (observation light) of the illumination light projected onto the eye E is guided along the right and left observation optical axes OR and OL via (the head lens 13 that is not shown and) the objective lens 15. Thus, the operator can binocularly observe a magnified image of the eye E. Symbols FL and FR shown in FIG. 8 denote a left observation field and a right observation field by the operator's microscope 6.

At this moment, part of the observation light, i.e., light near the optical axis O'R of the assistant's optical system, is reflected rightward by the reflecting member 50, thereby traveling along the optical axis O'R and entering the assistant's microscope 7. At this moment, the optical axis O'R includes a pair of right and left optical axes O'b and O'c as shown in FIG. 7. The optical axis O'b is an optical axis that passes the reflecting face 50b, and the optical axis O'c is an optical axis passes the reflecting face 50c. The observation light reflected by the reflecting face 50b is guided to the right ocular lens 53 as seen from the assistant. On the other hand, the observation light reflected by the reflecting face 50c is guided to the left ocular lens 53 as seen from the assistant. Thus, the assistant on the right side of the operator can binocularly observe a magnified image of the eye E.

The assistant, etc., moves the assistant's microscope 7 leftward as seen from the operator when necessary. Thus, the reflecting member 50 is rotated around the axis A by the gears 60 and 61 and the axial member 62, and is moved to the right side of the optical axis O (a position shown with the symbol "II"). At this moment, as shown with the arrow indicating both the sides in FIG. 6, the reflecting member 50 rotates so that the slope 50a passes above.

The gear ratio of the gears 60 and 61 is previously set so that a movement distance of the assistant's microscope 7 (a movement distance from right to left) corresponds to a rotation angle of the reflecting member 50 (a rotation angle from left to right: 90°). Further, in order to prevent the reflecting member 50 from further rotating from the state of the symbol "II" (rotating more than 90°), the gears 60 and 61 may have play (or, backlash, clearance). This configuration also applies to a case of rotating the assistant's microscope 7 in the opposite direction.

FIG. 10 illustrates an aspect when the assistant's microscope 7 is arranged on the left side as seen from the operator. In this case, as shown by a dotted line in FIGS. 6 and 8, the reflecting member 50 is arranged on the right side of the slope optical axis O.

Also in this state, the reflected light (observation light) of the illumination light projected onto the eye E is guided along the right and left observation optical axes OR and OL via (the not-shown head lens 13 and) the objective lens 15. Thus, the operator can binocularly observe the magnified image of the eye E. The observation fields at this moment are the regions shown with the the symbols FL and FR in FIG. 8, as are before the assistant's microscope 7 is moved.

Further, part of the observation light, i.e., light near the optical axis O'L of the assistant's optical system, is reflected leftward by the reflecting member 50, thereby travelling along the optical axis O'L and entering the assistant's microscope 7. At this moment, as shown in FIG. 7, the optical axis O'L includes the pair of right and left optical axes O'b and O'c. The observation light reflected by the reflecting face 50b is guided to the left ocular lens 53 as seen from the assistant. On the other hand, the observation light reflected by the reflecting face 50c is guided to the right ocular lens 53 as seen from the assistant. Thus, the assistant having moved to the left side of the operator can binocularly observe the magnified image of the eye E, as the assistant has been on the right side.

The assistant, etc., can move the assistant's microscope 7 rightward as seen from the operator when necessary. Then, the reflecting member 50 rotates in the direction opposite to the above and returns to the state shown in FIG. 9.

[Effect]

An effect of the surgical microscope 1 acting as described above will be explained.

The assistant's microscope 7 (the assistant's optical system) of the surgical microscope 1 is configured to be rotatable around an axis parallel to the optical axis O of the objective lens 15 (or around the optical axis O). Thus, the assistant, etc., can arrange the assistant's microscope 7 by switching it between two positions facing each other (the right side and left side of the operator). These two positions are equivalent to the "first position" and the "second position" of the present invention.

Further, the surgical microscope 1 is provided with the reflecting member 50 that reflects the observation light having propagated through the objective lens 15 in a direction different from the optical axis O (rightward or leftward). It is desired that the reflecting member 50 is disposed at a position retracted from the light path of the illumination light projected onto the eye E (observation object) and the light path of the illumination light entering the observation optical system 30.

Further, the reflecting member 50 has the slope 50a provided with the pair of reflecting faces 50b and 50c. The slope 50a is disposed so that an end thereof on the opposite side of the objective lens 15, which is an upper end thereof, (nearly) contacts a plane including the optical axis O, and is disposed so as to slant from the upper end toward the edge of the objective lens 15. Here, the plane including the optical axis O is a plane having a normal line in the same direction as the optical axis O'L (O'R) of the assistant's optical system.

Furthermore, the surgical microscope 1 is provided with the mechanism (the reflecting member drive mechanism) that rotates the reflecting member 50 around the axis A orthogonal to the optical axis O. This reflecting member drive mechanism includes the gears 60 and 61 and the axial member 62.

The axis A is located on the intersection line of a plane through the lower end of the slope 50a and orthogonal to the plane including the optical axis O (i.e., the lower face of the reflecting member 50: refer to FIG. 6, etc.) and the plane including the optical axis O.

The reflecting member 50 is rotated by this reflecting member drive mechanism, thereby being switched between the two positions symmetrical with respect to the surface including the optical axis O.

Thus, the reflecting member 50 acts so as to guide the observation light having propagated through the objective lens 15 to the assistant's microscope 7 switched to and arranged in the first position or the second position (the right or left side of the operator).

According to this surgical microscope 1, when switching the position of the assistant's microscope 7, it is possible to rotate the reflecting member 50 around the axis A and guide the observation light to the assistant's microscope 7 at a new position. Therefore, it is possible to change the position of the assistant's microscope 7 (the assistant's optical system) without blocking the observation fields of the operator.

Further, the surgical microscope 1 is configured so that the reflecting member 50 is automatically rotated in conjunction with switching of the position of the assistant's microscope 7. Therefore, it is possible to easily switch the position of the assistant's microscope 7.

To be specific, as compared with a conventional stereomicroscope in which the assistant's microscope 7 is once detached to switch the position, it is easy to switch the position.

Moreover, with the simple structure including the gears 60 and 61, the axial member 62, etc., it is possible to switch the position of the assistant's microscope 7.

Further, according to the surgical microscope 1, the right and left observation fields FR and FL of the operator's observation optical system 30 are arranged symmetrically with respect to the center of the objective lens 15 (with respect to the optical axis O). Therefore, the operator can observe the eye E from directly above. Thus, as compared with a conventional stereomicroscope for observing an observation object from a diagonal direction, it is possible to reduce burden on the operator.

Further, the surgical microscope 1 is configured to horizontally rotate the assistant's microscope 7. Therefore, it is possible to solve the problems of conventional stereomicroscopes in which the assistant's microscope is capable of swiveling upward, i.e., problems such as restriction on the shape of the lens tube and possibility of collision on an object above the lens tube, etc.

[Modification]

The configuration described in detail above is merely an example for implementing the stereomicroscope according to the present invention. Therefore, it is possible to modify arbitrarily within the scope of the present invention. An example of such a modification will be described below. Similar parts to those of the above embodiment will be denoted by the same symbols, regardless of whether they are shown or not shown in the drawings.

Figure 11:
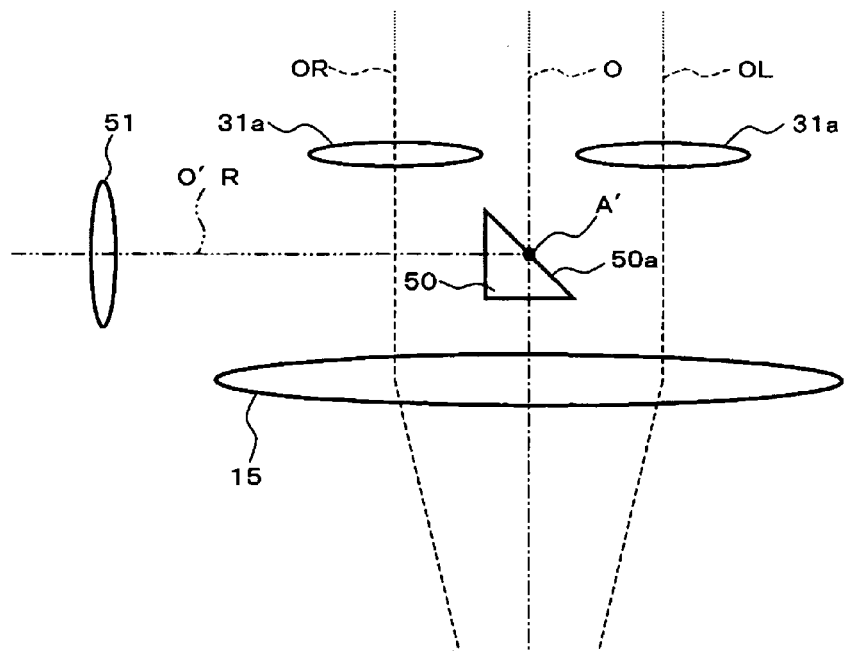
FIG. 11 is a schematic view for explaining the operation of a modification of the embodiment of the stereomicroscope (surgical microscope) according to the present invention.

The configuration of the modification of the abovementioned surgical microscope 1 is shown in FIG. 11. The abovementioned surgical microscope 1 is configured to rotate the reflecting member 50 by taking the right angle part of the cross-section of the reflecting member 50 as the axis, thereby guiding the observation light to the assistant's microscope 7 positioned right or left. But, in this modification, the reflecting member 50 is rotated with a different configuration.

A surgical microscope (a stereomicroscope) according to this modification is provided with a configuration similar to that of the above embodiment. However, the reflecting member 50 of this surgical microscope is disposed at a different position from in the above embodiment. That is, the reflecting member 50 is disposed so that an end of the slope 50a on the side of the objective lens 15 (i.e., a lower end) and an end of the slope 50a on the opposite side the objective lens 15 (i.e., an upper end) are positioned oppositely across a plane including the optical axis O.

Figure 12:
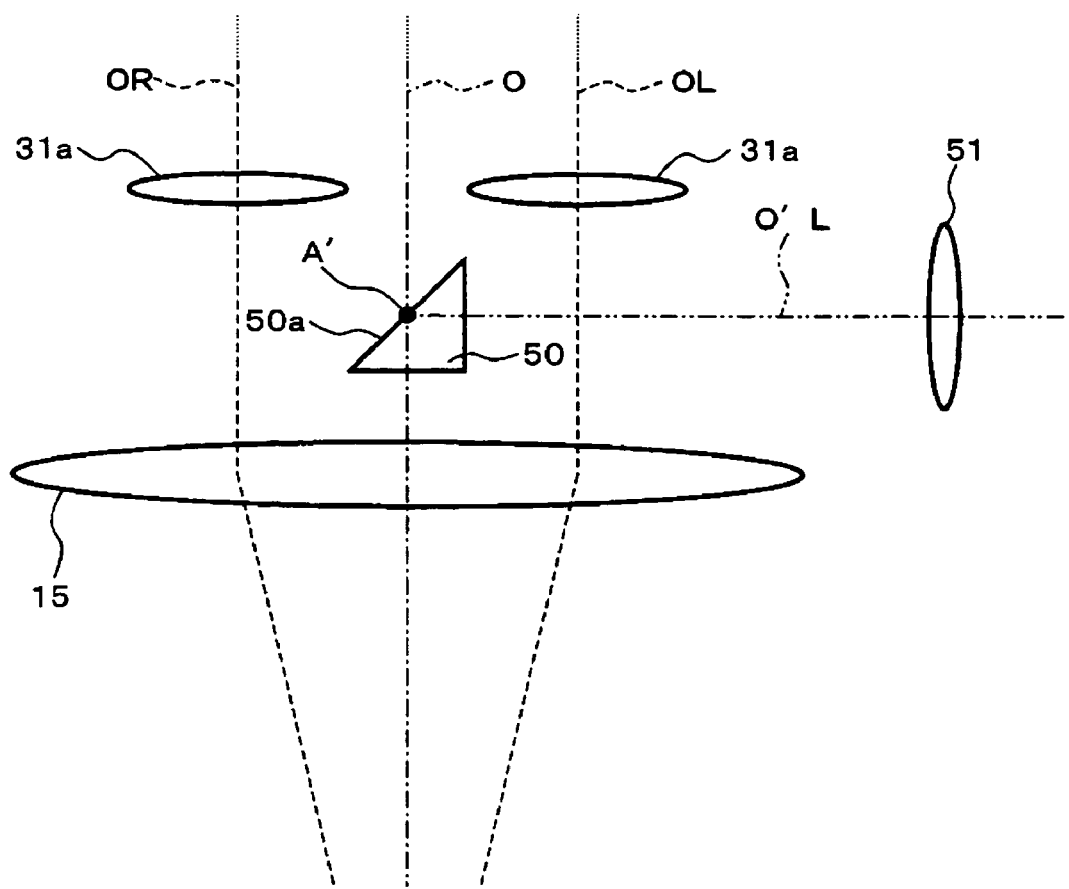
FIG. 12 is a schematic view for explaining the operation of the modification of the embodiment of the stereomicroscope (surgical microscope) according to the present invention.
Figure 13:
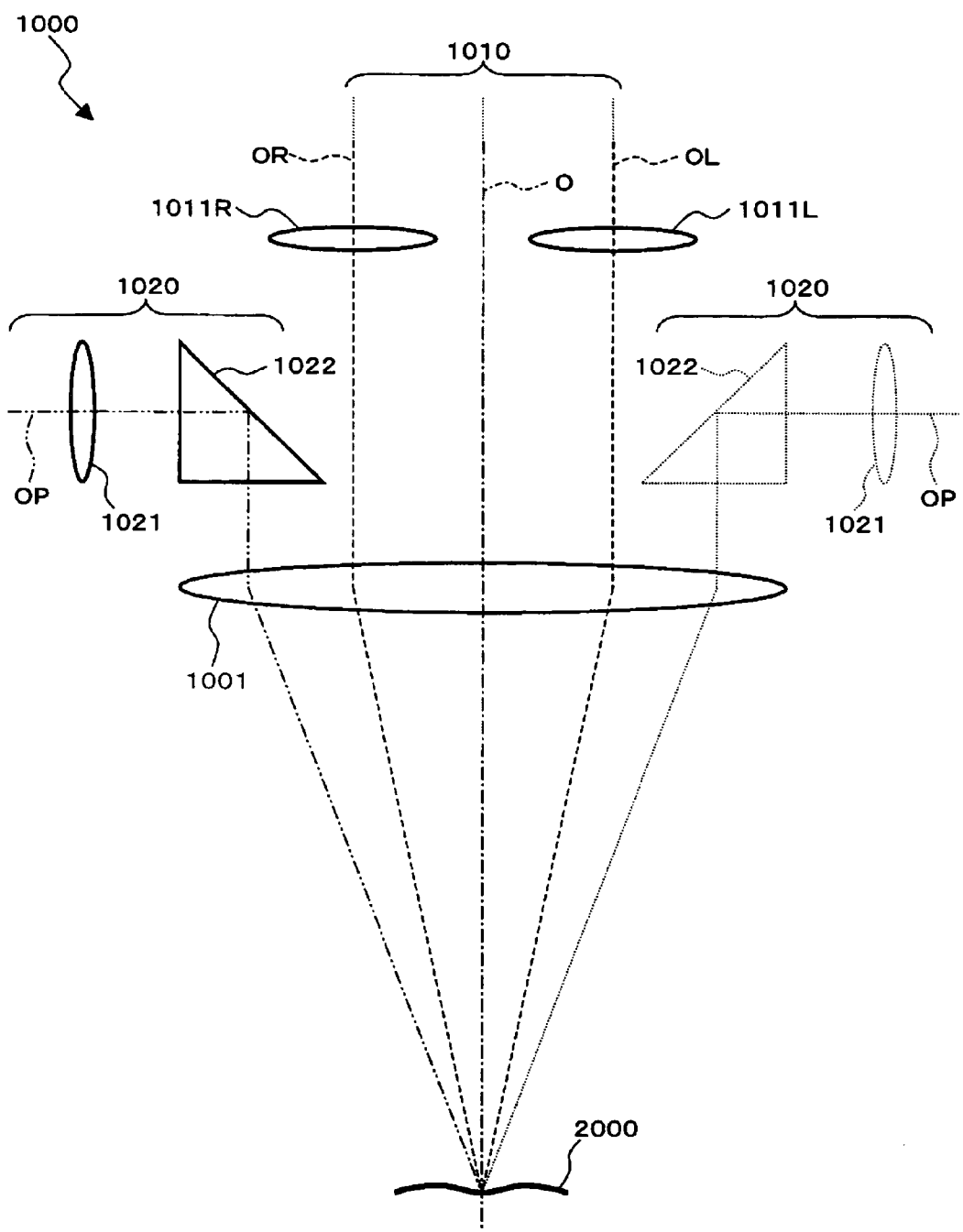
FIG. 13 is a schematic view illustrating part of the configuration of an optical system of a conventional stereomicroscope.
Figure 14:
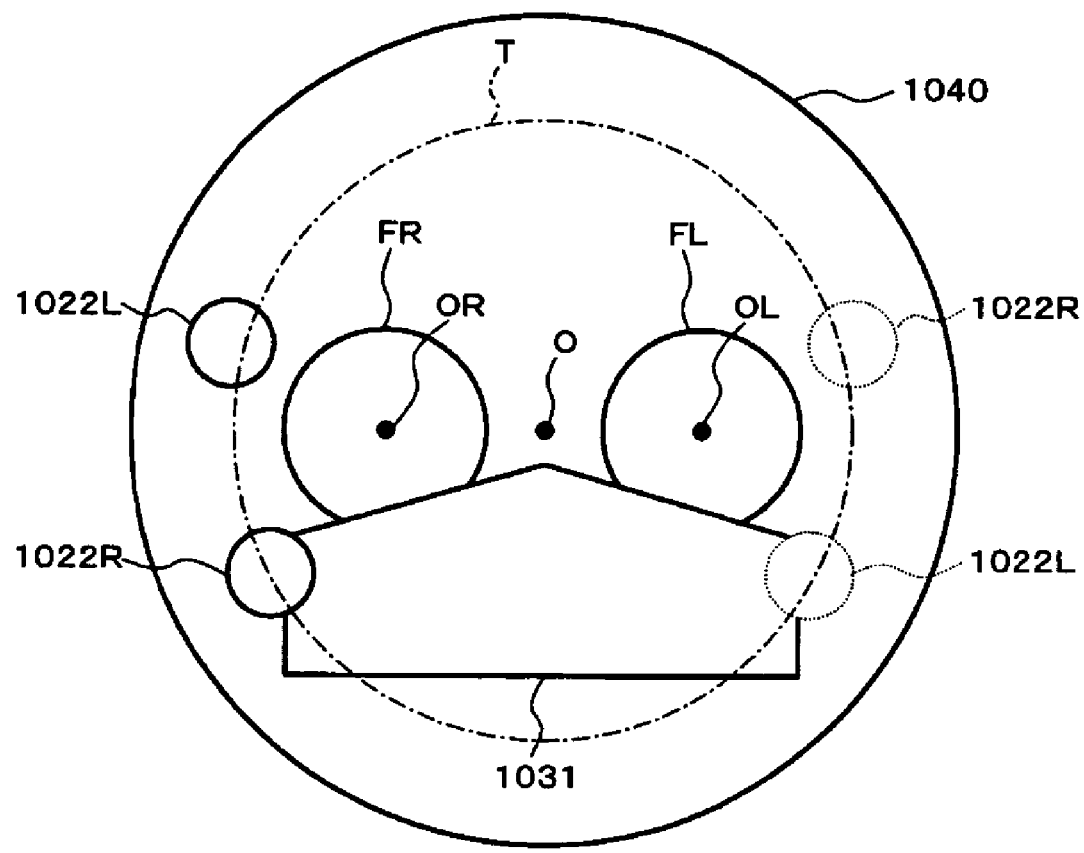
FIG. 14 is a schematic view illustrating part of the configuration of the optical system of the conventional stereomicroscope.

Here, the plane including the optical axis O is a plane extending in a direction orthogonal to paper of FIGS. 11 and 12 (more specifically, a plane having a normal line in the direction of the optical axis O'R (or the optical axis O'L) of the assistant's microscope 7). In the configuration shown in FIGS. 1 and 12, the slope 50a crosses the plane including the optical axis O at the central position of the vertical direction. As shown in FIG. 7, the slope 50a is provide with the right and left reflecting faces that reflect light having entered the reflecting member 50 (not shown).

Additionally, the surgical microscope according to this modification is provided with gears and an axial member that are similar to those of the above embodiment. More specifically, a gear similar to the gear 60 of the above embodiment is disposed on the inner wall face of the lens tube part 10. In addition, an axial member similar to the axial member 62 of the above embodiment is fixed to the intersecting part of the end face on the side of the illumination optical system 20 of the reflecting member 50 and the slope 50a. This axial member is disposed along an axis A' extending in the direction that connects the operator side and the side of the illumination optical system 20. This axial member is disposed so as to protrude from the reflecting member 50, for example. This axial member may be fixed on the slope 50a. More specifically, this axial member can be disposed at an arbitrary position off the light path of a light propagating through the reflecting face.

With such a mechanism (reflecting member drive mechanism), the reflecting member 50 is configured to be rotatable with the intersection line of the slope 50a and the surface including the optical axis O, i.e., the axis A', taken as the rotational axis. In particular, as shown in FIGS. 11 and 12, the reflecting member 50 is rotatable so that the slope 50a (right and left reflecting faces) is arranged symmetrically with respect to the plane including the optical axis O.

In a case where the reflecting member 50 is arranged as shown in FIG. 11 (the assistant's microscope 7 is positioned on the right side as seen from the operator), part of the observation light having propagated through the objective lens 15 (light near the optical axis O) is reflected by the right and left reflecting faces of the reflecting member 50 and is guided to the assistant's microscope 7. Thus, the assistant on the right side of the operator can observe the observation object with both the eyes.

The assistant, etc., moves the assistant's microscope 7 to the left side as seen from the operator when needed. Thus, the reflecting member 50 is rotated around the axis A' by the abovementioned reflecting member drive mechanism and is moved to the position shown in FIG. 12. At this moment, the reflecting member 50 rotates so that the slope 50a passes above.

The gear ratio of the reflecting member drive mechanism is previously set so that the movement distance of the assistant's microscope 7 (movement distance from the right to the left) corresponds to the rotational angle of the reflecting member 50 (90°).

In addition, in order to prevent the reflecting member 50 from further rotating from the state in FIG. 12 (rotating more than 90°), the gears may have a play. This configuration is also applied to a case of rotating the assistant's microscope 7 in the opposite direction.

When the assistant's microscope 7 is arranged on the left side as seen from the operator, the reflecting member 50 is arranged so that the slope 50a faces the upper right as shown in FIG. 12. In this state, the reflecting member 50 reflects part of the observation light having propagated through the objective lens 15 (light near the optical axis O) and guides it to the assistant's microscope 7. Thus, the assistant on the left side of the operator can binocularly observe the observation object.

When the assistant's microscope 7 is moved to the right side, the reflecting member 50 rotates in the direction opposite to the above and returns to the arrangement shown in FIG. 11.

According to this modification, when switching the position of the assistant's microscope 7, it is possible to rotate the reflecting member 50 around the axis A' and guide the observation light to the assistant's microscope 7 at a new position. Therefore, it is possible to change the position of the assistant's microscope 7 (the assistant's optical system) without blocking the observation fields of the operator.

Another modification will now be described. The assistant's microscope 7 may be manually rotated and moved by the assistant, etc., holding the assistant's microscope 7, or may be electrically rotated and moved in response to the operation with a specified switch. In the latter case, the switch is disposed to, for example, the lens tube of the assistant's microscope 7, the lens tube part 10 and the foot switch 8, and an optical system drive mechanism provided with an actuator such as a motor is disposed.

The operation of switching the direction of the reflecting member 50 may also be performed electrically by using the reflecting member drive mechanism provided with an actuator.

Further, it is not necessary to switch the direction of the reflecting member 50 in conjunction with the movement of the assistant's microscope 7, and it is possible to configure to separately perform the respective operations.

The shape of the reflecting member 50 is not limited to a triangular prism as in the above embodiment, and it may be an arbitrary shape. Moreover, two reflecting members may be separately disposed so that each of the reflecting members is provided with a reflecting face. In this case, the reflecting member drive mechanism acts so as to separately move the respective reflecting members.

In the above embodiment, the assistant's microscope 7 that enables binocular observation is used, but an assistant's microscope that enables only monocular observation may be applied. In this case, the reflecting member 50 is provided with a single reflecting face.

Moreover, an assistant's microscope that enables binocular observation and monocular observation by switching therebetween may be applied.

Further, in the above embodiment, the assistant's microscope 7 can be placed by switching it between two positions on the right and left, but the position (direction and number) where the assistant's microscope can be placed is arbitrary. When the assistant's microscope is placed at any position, the direction of the reflecting member is changed so as to guide the observation light to the assistant's microscope placed at the position.

In the above embodiment, the surgical microscope provided with the head lens 13 has been described. However, it is also possible to apply the present invention to a surgical microscope (stereomicroscope) without a head lens. Moreover, it is also possible to apply the present invention to an arbitrary stereomicroscope other than a surgical microscope for the ophthalmologic field.

What is claimed is:

1. A stereomicroscope, comprising:
an objective lens;
an illumination optical system configured to project an illumination light onto an observation object via the objective lens;
a first observation optical system configured to guide the illumination light reflected by the observation object and propagated through the objective lens to a first ocular lens;
a second observation optical system including a second ocular lens for observing the reflected light of the illumination light propagated through the objective lens;
an optical system drive mechanism configured to rotate the second observation optical system around an axis parallel to an optical axis of the objective lens, thereby switching and placing the second observation optical system between a first position and a second position facing each other;
a reflecting member disposed at a position retracted from both a light path of the illumination light projected onto the observation object and a light path of the reflected light entering the first observation optical system, and configured to reflect the reflected light propagated through the objective lens in a direction different from the optical axis; and
a reflecting member drive mechanism configured to rotate the reflecting member around a rotation axis orthogonal to the optical axis and guide the reflected light propagated through the objective lens to the second observation optical system placed at the first position or the second position.

2. The stereomicroscope according to claim 1, wherein:
the reflecting member has a reflecting face that is disposed obliquely to a plane including the optical axis, and that reflects the reflected light propagated through the objective lens; and
the reflecting member drive mechanism rotates the reflecting member so that the reflecting face is placed at symmetrical positions with respect to the plane.

3. The stereomicroscope according to claim 2, wherein:
the reflecting member has a slope that is disposed so that an upper end substantially contacts the plane, and that slants from the upper end toward an edge of the objective lens;
the reflecting face is disposed to the slope; and
the reflecting member drive mechanism rotates the reflecting member while taking an intersection line of the plane and a plane that passes a lower end of the slope and that is orthogonal to the plane as the rotation axis, thereby placing the reflecting face at the symmetrical positions.

4. The stereomicroscope according to claim 2, wherein:
the reflecting member has a slope with an upper end and a lower end placed on a side opposite to the plane;
the reflecting face is disposed to the slope; and
the reflecting member drive mechanism rotates the reflecting member while taking an intersection line of the plane and the slope as the rotation axis, thereby placing the reflecting face at the symmetrical positions.

5. The stereomicroscope according to claim 1, wherein:

the reflecting member drive mechanism rotates the reflecting member in conjunction with switching of a position of the second observation optical system by the optical system drive mechanism.

6. The stereomicroscope according to claim 5, wherein:

the optical system drive mechanism has a first gear that is disposed along a rotation direction of the second observation optical system and rotates with the second observation optical system; and the reflecting member drive mechanism has an axial member that is disposed along the rotation axis and connected to the reflecting member, and a second gear that is connected to the axial member and engaged with the first gear to rotate the axial member with the reflecting member in accordance with rotation of the first gear.

7. The stereomicroscope according to claim 1, wherein:

the second ocular lens includes a pair of right and left ocular lenses;

the second observation optical system includes a left observation optical system that guides the illumination light propagated through the objective lens to the left ocular lens, and a right observation optical system that guides the illumination light to the right ocular lens;

the reflecting member has a pair of right and left reflecting faces; and the reflecting member drive mechanism rotates the reflecting member, thereby guiding the reflected light reflected by the left reflecting face to the left observation optical system, and guiding the reflected light reflected by the right reflecting face to the right observation optical system.

* * * * *